United States Patent [19]
Sibalis

[11] Patent Number: 4,900,414
[45] Date of Patent: Feb. 13, 1990

[54] COMMERCIAL SEPARATION SYSTEM AND METHOD USING ELECTROKINETIC TECHNIQUES

[75] Inventor: Dan Sibalis, Stony Brook, N.Y.
[73] Assignee: Drug Delivery Systems Inc., New York, N.Y.
[21] Appl. No.: 234,258
[22] Filed: Aug. 19, 1988
[51] Int. Cl.$^4$ ............................................. G01N 27/26
[52] U.S. Cl. .............................. 204/180.1; 204/182.7; 204/182.8; 204/182.9; 204/299 R
[58] Field of Search ............. 204/299 R, 182.8, 182.7, 204/182.9, 180.1, 182.1, 182.3

[56] References Cited
U.S. PATENT DOCUMENTS
3,888,758  6/1975  Saeed ............................... 204/299 R Primary Examiner—John F. Niebling
Assistant Examiner—John S. Starsiak, Jr.
Attorney, Agent, or Firm—Lackenbach, Siegel Marzullo & Aronson

[57] ABSTRACT

A commercial electrokinetic separation system extracts charged particles from fluids and separates the particles into discrete separation bands. An electrokinetic column of extended length has a plurality of alternatingly spaced layers of electrokinetic material and electrodes along its length. A traveling wave electrical field is established by applying an electrical potential between two adjacent or nearly adjacent electrodes at one end of the column and by moving the connections progressively to electrodes further along the column, working toward the other end. A fluid containing particles for separation is introduced in a chamber at said one end of the column where the traveling wave is initiated and particles having a phoretic speed equal or greater than the velocity of the traveling wave move from one end to the other end of the column, leaving behind all particles which have lesser phoretic speeds. The electrical source can be either AC or DC. Both negatively charged and positively charged particles may be separated from the fluid in separate sweeps of the traveling wave field when wave velocity corresponds to the particles's phoretic speed. Isoelectric and isotachophoresis focusing can be incorporated to separate different charged materials which have the same polarity of charge and the same phoretic speed.

36 Claims, 7 Drawing Sheets

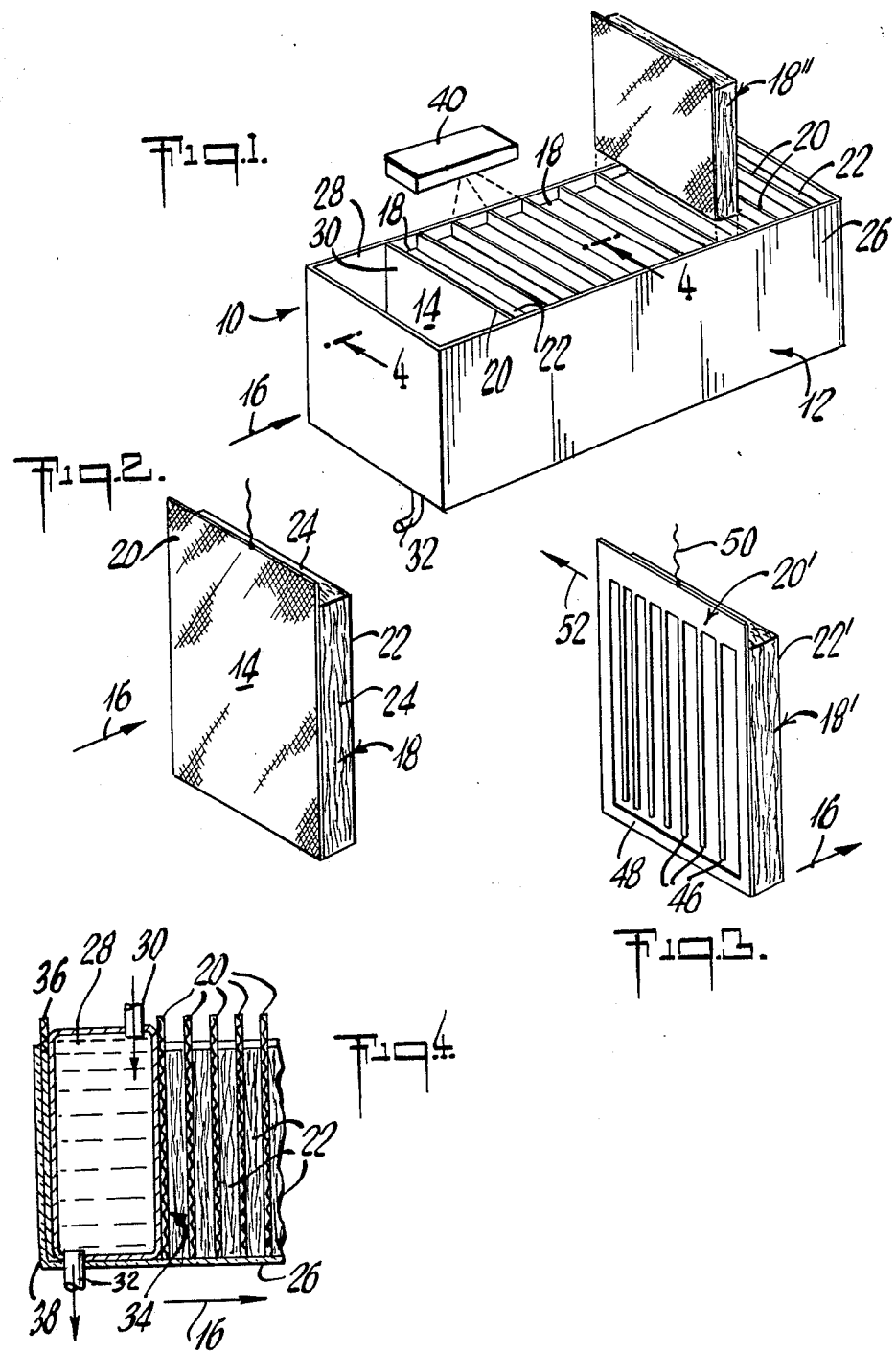

COMMERCIAL SEPARATION SYSTEM AND METHOD USING ELECTROKINETIC TECHNIQUES

BACKGROUND OF THE INVENTION

This invention relates generally to the separation of particles and substances from a fluid and more particularly to an apparatus using electrokinetic phenomena in commercial applications for extracting known substances from a fluid or for purifying substances by removal of certain materials.

Charged particles and substances suspended or dissolved in a fluid can be made to move under the influence of an electrical field, one such phenomenon being known as electrophoresis. The speed of movement of a charged particle or substance in an electrokinetic medium in a given electric field, which speed is known as its phoretic speed, is generally dependent on the particle's mass, size, and magnitude of electrical charge. These qualities are specific to each particle and substance as it relates to a specific electrochemical environment. Electrophoresis is well-known and widely used in separation and analysis of compounds present in a fluid. However, the existing art is primarily related to laboratory research and testing, for example, in medical and chemical analysis, and is not applied to commercial quantities of materials. In the existing laboratory art, an electrophoretic element or column generally is a strip or column of wet paper, silica powder or a hydrogel, the column being loaded with a fluid which is to be analyzed for the presence of particular particles and substances. The charged particles and substances may include ions, molecules, compounds, polypeptides, blood cells, etcetera. In the following description, the word "particle" is intended to denote any such material.

When a DC voltage is applied at opposite ends of an electrophoretic element, an electric current flows therethrough. An electrical field is created which causes charged particles in the fluid to migrate with respective phoretic speeds toward the electrodes and to thereby separate into discrete separation zones or bands in the process. The materials in each discrete band can be analyzed for identification and quantification.

However, this process has disadvantages. One disadvantage is that long electrophoretic columns are required to achieve separation, and use of high voltages may be required since different types of particles may resolve into distinctive groups very slowly when their electrophoretic speeds are similar.

Another disadvantage results from electric current which flows through the electrodes at the ends of the electrophoretic element or column. This current, which is limited by using, when possible, lower conductivity column materials, flows the entire length of the column and produces heating of the fluid. A coolant may be required to prevent overheating and evaporation of the fluid and distortion of the separation bands. All these effects generally limit the efficiency and accuracy of the analyzing process. A narrow, high resolution particle separation zone is very difficult to provide and maintain.

A further disadvantage of such prior art laboratory technology is that opposite polarity particles cannot be separated by loading the column at one end.

Because of the high cost and technical limitations, electrokinetic techniques as now used are capable of separating only very small amounts of particles, making the end product very expensive and heretofore impractical for use with commercial quantities of materials. The prior art does not disclose a method or apparatus for a continuous process used for commercial extraction of materials from fluids.

What is needed is a commercial separation system and method using electrokinetic techniques which is useful in purifying fluids and extracting substances from the fluids for the sake of the extracted substance, without the problems of slow performance, extended chamber length, high voltages and resultant heating and evaporation of column fluids.

SUMMARY OF THE INVENTION

Generally speaking, in accordance with the invention, a commercial separation system and method using electrokinetic techniques, especially suitable for commercial operation for extracting substances from a fluid mass, for purposes of extraction or purification, is provided. In one embodiment, an electrophoretic column or member of extended length and large flow cross-section is provided. A plurality of electrodes, spaced apart one from the other, are positioned along the column length, the electrodes having a cross-section corresponding with the column cross-section. Thus, the electrodes divide the column into a series of segments, each segment being an electrophoretic cell, the segments being stacked, like the pages of a book, to form an extended column.

A traveling wave electrical field is established by applying an electrical potential between two adjacent or nearly adjacent electrodes at one end of the column and by moving the connections progressively to electrodes further along the column, working toward the other end. A fluid containing particles and substances for separation is introduced continuously at the column end where the traveling wave is initiated and particles and substances having a phoretic speed equal to or greater than the velocity of the traveling wave move from the one end of the column to the other end of the column, leaving behind all particles and substances which have lesser phoretic speeds.

For given materials and electrical potentials, known substances will travel a known determined distance along the column length in a predetermined time period. At that position along the column, the substance of interest may be removed from the column.

The electrical source for powering the electrodes can be either AC or DC. Both negatively charged and positively charged particles can be separated from the incoming fluid flow in separate sweeps of the traveling wave electrical field when the wave velocity corresponds to the particle's phoretic speed. Isoelectric and isotachophoresis focusing techniques can separate different charged materials which have the same polarity of charge and the same phoretic speed.

Accordingly, it is an object of this invention to provide an improved commercial separation system and method using electrokinetic techniques which do not apply a voltage over an electrokinetic column's entire length at one time.

Another object of this invention is to provide an improved commercial separation system and method using electrokinetic techniques which allow continuous feed of the fluid to be processed.

A further object of this invention is to provide an improved commercial separation system and method using electrokinetic techniques which reduce heating and evaporation from the electrolyte in the electrokinetic medium.

Still another object of this invention is to provide an improved commercial separation system and method using electrokinetic techniques which use low voltage in operation of an electrokinetic column.

Yet another object of this invention is to provide an improved commercial separation system and method using electrokinetic techniques which separate charged substances from a fluid and bring the charged substances to a preselected location for removal from the system.

A further object of this invention is to provide an improved commercial separation system and method using electrokinetic techniques which can be automated and constructed with integrated circuitry and be preprogrammed by computer.

Another object of this invention is to provide an improved commercial separation system and method using electrokinetic techniques which provide field equalization in an electrokinetic separation column.

Still another object of this invention is to provide an improved commercial separation system and method using electrokinetic techniques which provide high density concentration of separated substances prior to removal from the system.

Still other objects and advantages of the invention will in part be obvious and will in part be apparent from the specification.

The invention accordingly comprises the several steps and the relation of one or more of such steps with respect to each of the others, and the apparatus embodying features of construction, combination of elements and arrangement of parts which will be adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of the commercial separation system using electrokinetic techniques in accordance with the invention;

FIG. 2 is a perspective view of a single segment of the commercial separation system using electrokinetic techniques of FIG. 1;

FIG. 3 is an alternative embodiment in accordance with the invention, in perspective, of a segment for the commercial separation system using electrokinetic techniques of FIG. 1;

FIG. 4 is a partial elevational view in section, taken along the line 4—4 of FIG. 1;

DESCRIPTION OF THE PREFERRED EMBODIMENTS

Figure 5A:
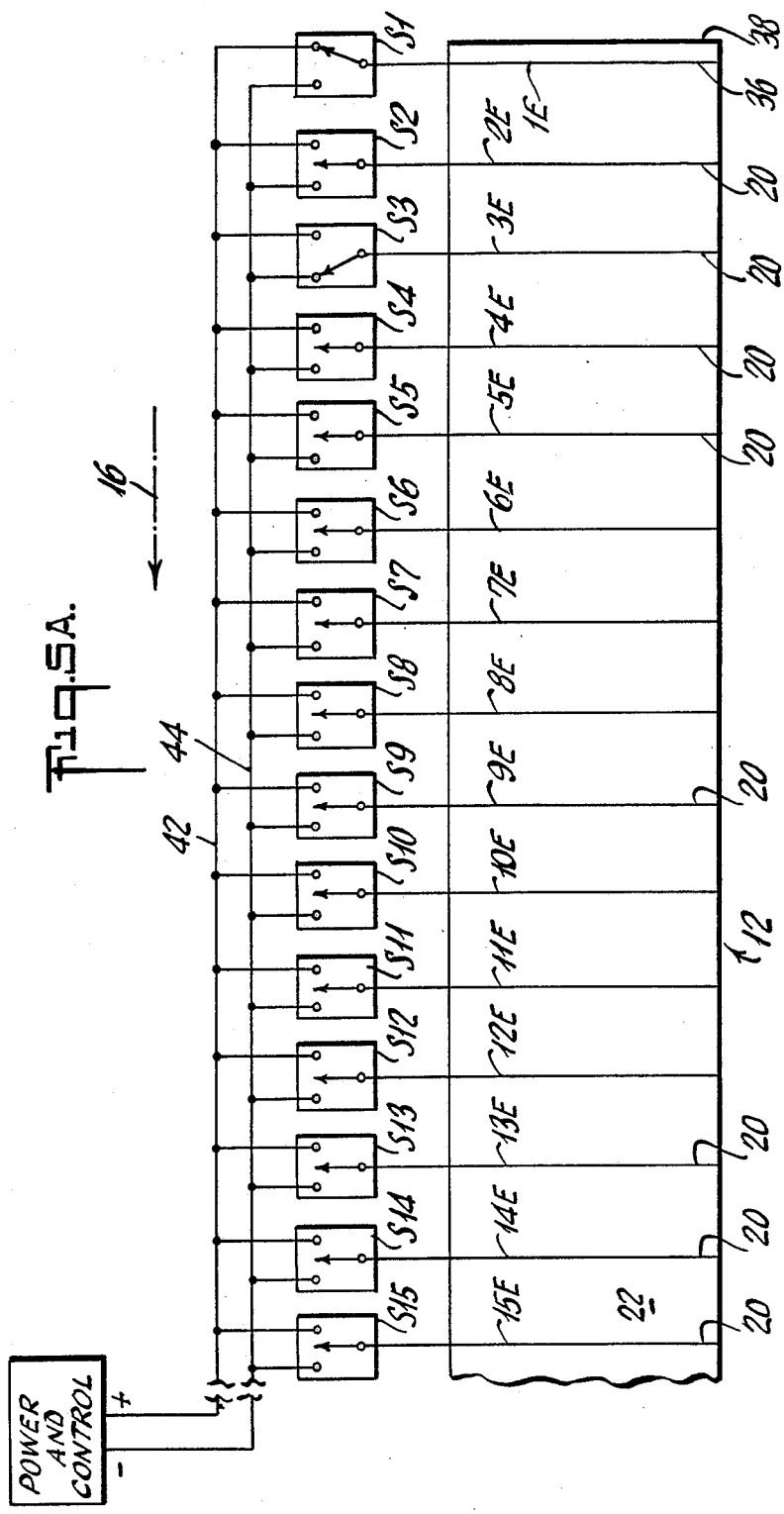
FIGS. 5A-5C are fragmented semi-schematic views showing steps of operation and switch positions in the commercial separation system and method using electrokinetic techniques in accordance with the invention.

With reference to FIGS. 1, 3 and 4, a commercial separation system 10 and method using electrokinetic techniques in accordance with the invention is a box-like structure 12 of extended length and having height and width to provide a large cross-sectional flow area 14 transverse to the direction indicated in the Figures by the arrow 16. A plurality of segments 18 are stacked end-to-end in the lengthwise direction 16 of the structure 12. The stack of segments 18 may be analogized to modular building blocks or pages in a book, and the length of the structure 12 can be adapted to suit the particular application.

Each segment 18 includes an electrode 20 and a layer of electrokinetic material 22, for example, electrophoretic material. The electrophoretic material may be a gel, filter paper, or other inert porous material, such as purified blotter paper, holding an electrolyte fluid. Such materials are conventionally available for electrophoretic columns. The edge surfaces 24 of the electrokinetic material 22 are sealed, for example, using heat, so as to create effectively a container holding the electrokinetic material 22.

The electrodes 20 are made of electrically conductive material, for examples, metal, electroconductive plastics, carbon such as graphite, or a carbon compound, in a porous construction which allows for flow of materials through the face 14 of the electrode in the direction of the arrow 16 as explained more fully hereinafter. The electrodes 20 may also be a porous material, for example, paper or cloth with graphite printed on the surface. The electrodes 20 are in electrical contact with the electrokinetic material 22 on both face surfaces of the electrodes 20 when the segments 18 are stacked face-to-face as illustrated in FIG. 1. In FIG. 1, the electrodes 20 are uniformly spaced one from the other as the electrokinetic material layers 22 are of uniform thickness. It should be understood that in an alternative embodiment of a commercial separation system using electrokinetic techniques in accordance with the invention, the thickness of the electrokinetic material 22 in each segment 18 may differ from segment to segment thus giving a variable spacing between the electrodes 20.

The stack of segments 18 is enclosed in a housing 26 fabricated of electrically non-conducting material or coated for the purpose of non-conduction, the housing material being nonreactive with the electrolyte of the electrokinetic material 22 and the substances which are of interest in operation of the system 10.

The segments 18 are clamped together in a lengthwise direction to assure good electrical contact. Preferably the system 10 is constructed such that selected segments 18, as suits a particular application, are adapted for removal from the system 10 without disturbing other segments 18 in the system as illustrated for segment 18" (FIG. 1).

The housing 26 provides an input plenum chamber 28 into which a fluid to be processed is input by means of an input pipe 30 and output by means of an output pipe 32, so that a continuous flow through the input plenum chamber 28 is possible. The interface 34 between the stack of segments 18 and the contents of the input plenum chamber 28 is porous, such that any liquid in the plenum chamber 28 is in electrical contact with the first electrode 20 of the stack of segments 18.

Additionally, a starting electrode 36 is positioned on the end wall 38 of the housing 26, such that fluid in the input plenum chamber 28 forms a layer between the starting electrode 36 and the first segment electrode 20. The electrode 36 is electrically insulated from the housing 26.

As explained more fully hereinafter, a power and control unit 40 directs energy to the system 10 and controls timing as described hereinafter to effect operation. Control of the system by the power and control unit 40 is representationally illustrated by broken lines between the control unit 40 and the structure 12.

FIGS. 5A-5C and 6 are semi-schematic representations of the system 10. For convenience in explaining operation of the system, the electrodes 20, 36 are also identified numerically starting in the input plenum chamber 28 with electrode 36 being identified as 1E, the first electrode 20 being identified as electrode 2E, the next electrode 20 is identified as 3E and so on to the end of the stack of segments 18. The actual number of electrodes E can vary with the application. Therefore the last electrode in a complete stack is nE in the discussion herein.

It will be apparent to those skilled in the electrokinetic arts, that if a DC voltage potential is applied between the first electrode 1E and a last electrode nE, then an electrical current will flow through the entire length of the stack of segments 18, that is, along the length of the structure 12. Ideally, current will be distributed across the entire flow area 14 of each segment 18. Negatively charged particles in the structure or column 12 will migrate toward the electrode connected to the positive terminal of the power source, whereas positively charged particles in the column 12 will migrate toward the negative terminal of the DC power source as is conventional in electrokinetic processes. This operation will have the disadvantages described above in that current flows continuously through the entire length of the column. This tends to evaporate solvents in the electrokinetic medium, unless cooling means are provided. Heating distorts the separation bands which are produced, containing different charged particles, and in general, substantially limits the feasible resolution and efficiency of the process.

Particles which are suspended in the column 12 move under the influence of the electric field and velocity of particle motion is specific in that medium to the particular particle, which may be an ion, molecule, compound, etcetera. In the process, the faster moving particles separate from the slower moving particles and discrete bands or zones of particular particles are formed. The substances in the separated bands are subject to removal from the system 10 independently of the other particles with an effectiveness of the entire system depending upon the effectiveness of the electrokinetic process to provide separation of bands.

As explained more fully hereinafter, the subject invention with its array of electrodes 1E-nE along the length of the electrokinetic member 12 effectively divides the column 12 into a plurality of shorter but interconnected columns. A DC electrical potential is placed across a pair of closely spaced electrodes near the inlet plenum chamber 28 causing movement of charged particles between those connected electrodes. Then, as moving particles approach an electrode to which the DC potential is applied, the potential is switched to another set of electrodes farther along the column 12, that is, farther away from the input plenum chamber 28. In effect, a traveling wave electrical field is created which moves from one end of the electrokinetic column 12 to the other. Synchronous movement is created in those particles having a specific phoretic speed which is the same or higher than the speed of the traveling wave along the column 12. Such charged particles are trapped within the traveling wave, whereas particles, whose phoretic speed is less than the speed of the traveling field, are left behind in time in a region without a voltage gradient.

The traveling wave can be reintroduced at the start of the column 12 to move at a slower velocity along the length of the column, such that charged particles previously left behind, are now separated from an inputted fluid. Repeated traveling waves of constant velocity may be used to increase the effective separation of a particular substance or charged particle. Both positively and negatively charged particles may be separated and moved to selected regions respectively in the commercial separation system and method using electrokinetic techniques in accordance with the invention, whereas in the prior art one polarity of charged particles collects at one electrode at one end of the column and oppositely charged particles collect at the other end of the column.

Generation of the traveling wave electric field by application of electrical potential to the electrodes 20, 36 in proper sequence, is accomplished by the power and control unit 40. The power and control unit 40 may include a programmable microprocessor, voltage and current regulators, timing means, switching networks, etcetera, as are necessary to provide the traveling wave electrical field in the desired velocity of travel along the column and with desired voltages, repetition rates and polarities to separate substances and particles of interest. The electronic circuitry, commercially available for such purposes, is not a novel portion of this invention, and accordingly is not described in detail herein.

Figure 5B:
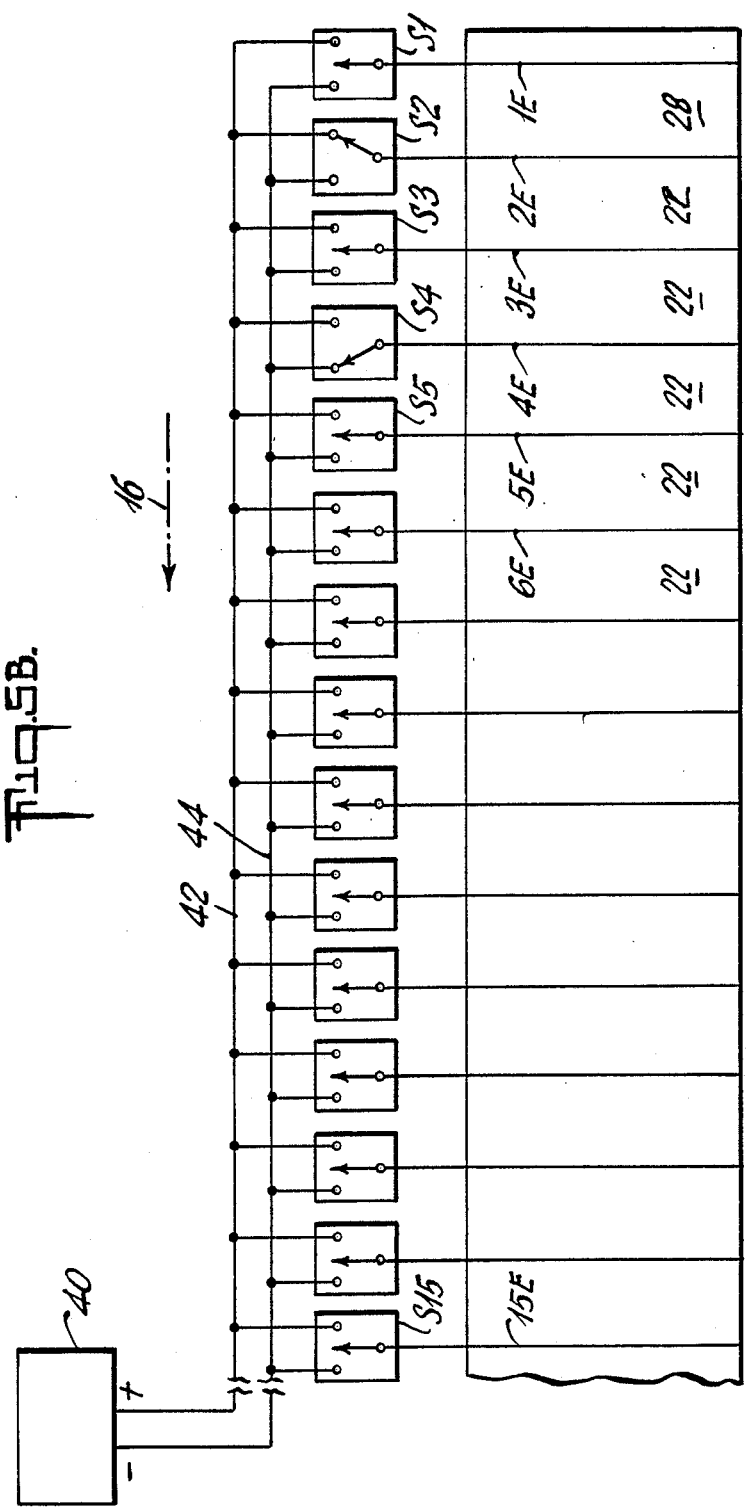
Figure 5C:
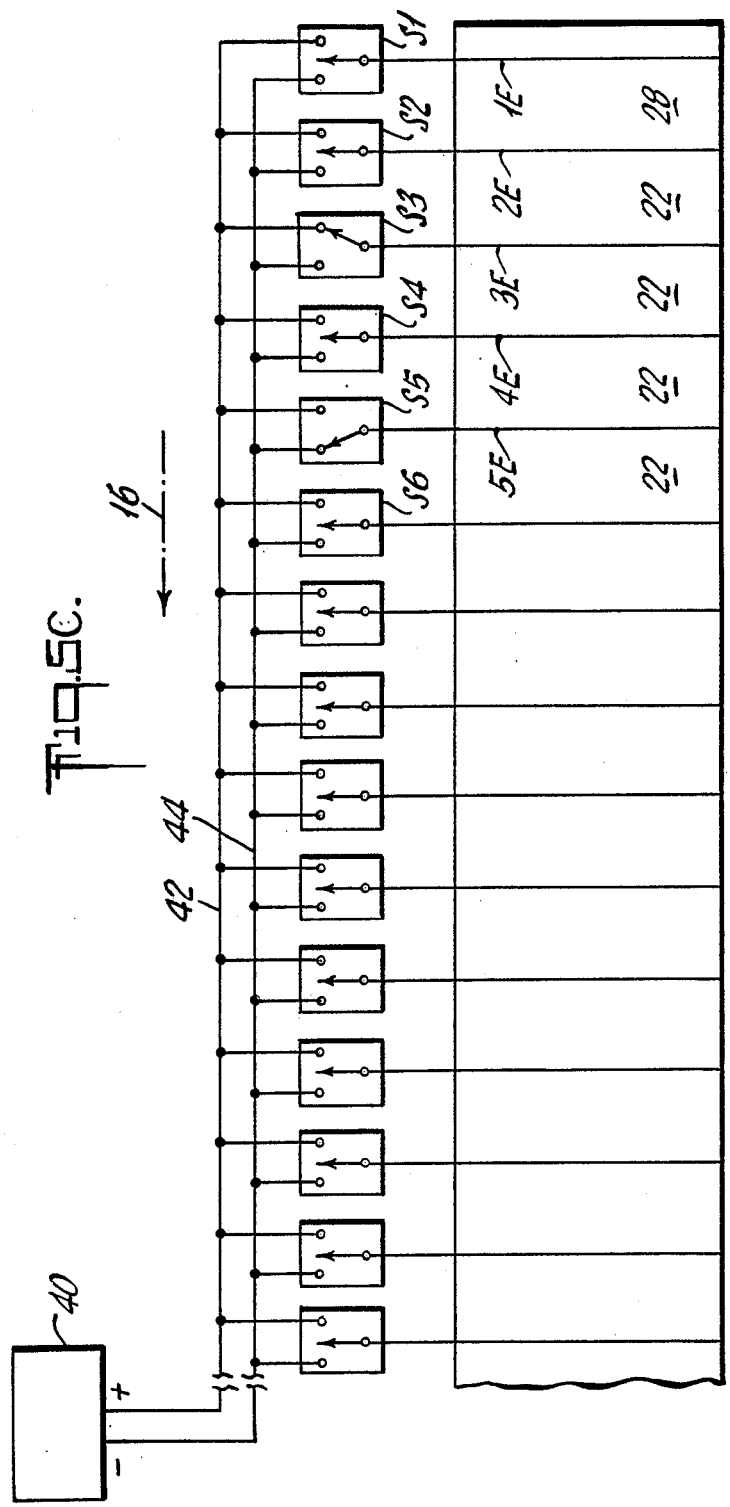

FIG. 5A is a semi-schematic and functional diagram of the commercial separation system and method using electrokinetic techniques in accordance with the invention showing interconnections between the power and control unit 40, electrodes 1E-nE (electrodes beyond 15E are not shown). The structure indicates the transverse positioning of the electrodes 1E, etcetera and the electrode 36 in relationship to the direction of flow as indicated by the arrow 16. For simplicity in illustration and explanation of the operating principles, FIGS. 5A-5C show the electrodes with single width lines.

As illustrated, the power and control unit 40 provides DC output with positive potential applied to the bus 42 and negative potential applied to the bus 44. Each electrode 22, 36 connects to the pole of a single pole, three-position switch S having one position connected to the positive bus 42, another position connected to the negative bus 44, and a central neutral or floating position not connected to either bus. For convenience, the switches are numbered S1, S2 ... Sn with the numerical portion of the identification corresponding with the numerical portion of the associated electrode identification 1E, 2E, ... nE.

Such electromechanical switches as illustrated in FIGS. 5A–5C and FIG. 6 are cumbersome and inconvenient, requiring manual or electromechanical operation and are used here merely for illustrating operating principles of the system. Such switches are readily replaced for commercial purposes by solid state switches. Such solid state circuitry is well-known and is not considered to be a novel portion of this invention.

Operation of the commercial separation system 10 and method using electrokinetic techniques in accordance with the invention illustrated in the Figures, is now explained. The system receives a continuous flow of fluid from which substances are to be removed in a process of extraction for commercial purposes or for purification of the parent flow material. The fluid enters the input plenum chamber 28 through the input pipe 30 and, after flowing over the surfaces of the electrodes 1E, (36), 2E (20), exits the chamber 28 through the output pipe 32.

To start an extraction or purification process, the switch S1 is connected to the positive output of the power and control unit 40 and the terminal of the switch S3 is connected to the negative output of the power and control unit 40. Thus, a current flows from the positive electrode 36 through the process fluid, and the electrolyte of the electrokinetic material 22 to the electrode 3E, through the switch S3, and to the negative terminal of the power and control unit 40.

It should be understood that the polarity selected for description here, that is, positive on electrode 1E and negative on electrode 3E, are exemplary but would be particular to a selected input fluid and the substance which is to be extracted therefrom. It should be noted that the other switches are in the neutral position, that is the electrodes 2E, 4E-15E are not connected to any electrical potential. Conventional DC current from the positive terminal to the negative terminal is used in the above description.

With the potentials on electrodes 1E, 3E as indicated in FIG. 5A, positively charged particles and substances in the fluid within the plenum chamber 28 are attracted toward the negatively charged electrode 3E. These particles and substances pass through the porous electrode 2E and migrate into the electrokinetic material 22 between the electrodes 2E-3E. Negatively charged particles in the fluid in the chamber 28 migrate toward the positively connected electrode 1E.

As the positively charged particles from the plenum chamber 28 approach the negatively connected electrode 3E, the connections at the switches S1–S4 are changed to produce the condition shown in FIG. 5B. In particular, switch S1 is disconnected from the positive bus 42 and is allowed to float. Switch S2 is changed from a neutral position to a connection with the positive bus 42; switch S3 is changed from connection to the negative terminal 44 to a neutral, floating condition, and switch S4 is changed from a neutral condition to connection with the negative bus 44. All other switches remain in the neutral position.

Thus the voltage gradient, which formerly existed between electrodes 1E and 3E, is moved with the same polarity to exist between electrodes 2E and 4E. In other words, a voltage wave is traveling in the direction of the arrow 16 along the column 12.

Now, positively charged substances and particles which were approaching electrode 3E continue through the porous electrode 3E being attracted toward electrode 4E. The negative particles in the plenum chamber 28 which were attracted toward electrode 1E, now reverse direction and are attracted toward electrode 2E.

As positively charged particles approach the electrode 4E, the power and control unit 40 again adjusts the switch positions to create the condition illustrated in FIG. 5C. In particular, switch S5 is moved from a neutral position to connect electrode 5E to the negative bus 44; switch S4 is shifted from its connection to the negative terminal 44 to the neutral position; switch S3 is switched from a neutral position to connection with the positive bus 42 and switch S2 is switched from connection to the positive bus 42 to a neutral position. All other switches are set to the neutral position.

Thus, the electrical potential wave which is attracting positively charged particles and substances, provides a voltage gradient of the same polarity between electrodes 5E and 3E which had previously existed between electrodes 4E and 2E, and earlier between electrodes 3E and 1E. In this way, the traveling potential wave continues to move in the direction indicated by the arrow 16. The positive particles which in FIG. 5B were approaching electrode 4E, now continue and approach electrode 5E. The negative particles which in FIG. 5B were located in plenum chamber 28 and approaching electrode 2E, remain in chamber 28 where no electrical potential gradient exists as both electrodes 1E and 2E, are set to a neutral position.

The process of switching electrode potentials is continued so that the wave travels in the direction of the arrow 16 until the particle or substance of interest is adequately separated from other particles of the same polarity. The number of switching steps and the number of elements 18 required for satisfactory separation is determined based on the fluid inputted, the particles or substances of interest, and the electrokinetic material 22, etc. It should be noted that the switching is accomplished with timing corresponding with the phoretic speed of a particle or substance of interest. Thus, substances and particles with lower phoretic speeds are left behind. For example, slower moving positive particles which in FIG. 5B are found between electrodes 2E and 3E are left behind when the condition of FIG. 5C is established. In this situation, the slower moving positive particles between electrodes 2E and 3E are repelled from the now positively connected electrode 3E and consequently, never advance down the column during this electrical potential wave.

After the potential wave has traveled the predetermined distance for separation of preselected charged particles, a second identical wave may be passed through the structure 12. Repetition of the wave will gather more particles of interest and bring them to the selected segment 18. Additionally, new potential waves at different phoretic speeds can pass through the column and other particles of slower phoretic speed can be moved to a selected segment 18. Also, after a sufficient time lapse, the polarities in the potential wave can be reversed so that oppositely charged particles can be moved in the direction of the arrow 16 for extraction or separation. The substances of interest, when concentrated in a particular segment 18, can be removed from the system by removal of the entire segment 18, including its electrode 20 and electrokinetic material 22.

While the process described above includes a continuous flow of fluid through the input plenum chamber 28, the process can be operated on batches of fluid which fill the plenum chamber 28, and are held in the chamber while one or more electrical potential waves of proper polarity, voltage and linear velocity are passed through the system 10. Additionally, it should be understood that the effluent from the input plenum chamber 28 through the output pipe 32 can provide the input to another system 10 identical to that described, the second system operating with an input fluid of lower concentration of the substance of interest than does the first system 10. Also, fluid exiting the plenum chamber 28 can be recycled in part or in toto back to the chamber 28 in a continuous flow process.

In the preceding description, electrodes which were simultaneously connected to the power source 40 had one intervening electrode between them which was in a neutral or floating condition. By having an intermediate electrode set to the neutral position of the switch, the field across the face area 14 of the column 12 is maintained in alignment and uniform, whereas when the voltage is applied to adjacent electrodes, the field may become distorted and non-uniform. Because the intermediate electrode is an electrical conductor, a uniform potential is reestablished in the width and height directions of the column 12.

Supplemental electrodes may be provided which need never be connected to switch means or to the power source. These supplemental electrodes (not shown) reestablish a uniform field when these supplemental electrodes intervene between electrodes of an electrically connected pair of electrodes as the field travels the column 12. The number of intervening electrodes between activated electrodes need not be limited to one. Any number of intervening electrodes or no intervening electrodes may be used as suits the particular application. Also, changing the thickness of the electrokinetic materials 22 in different segments 18, will change the physical velocity of the electrical field, although the switching rates may remain unchanged.

In summary, the rate at which the traveling potential wave moves down the electrokinetic column 12 is made to match the phoretic speed of the particle of interest. The wave travels at a velocity corresponding to that phoretic speed, such that the wave "captures" the charged particles and they move in synchronism. The particles of interest are not necessarily the particles with the highest phoretic speed. In such case, the particle with the highest phoretic speed will move faster than the traveling potential wave and may react at the electrode when contact is made and thereby be removed from the process. The traveling voltage wave can be repeated several times with the same velocity down the structure 12 commencing with the condition indicated in FIG. 5A, such that more effective separation of particles of interest is made from the fluid input to the plenum chamber 28. Different voltage levels may be applied at different column distances to effect different velocities.

Operation of the system by applying a potential between a pair of electrodes E which are adjacent to each other, or spaced apart by one or two electrodes E, causes a current to flow only between the two electrodes connected to the power source. This is in contrast to conventional electrokinetic columns, where a voltage is applied across the entire length of the medium in order to produce the same voltage gradient which is effective in the construction of the subject invention.

Thus, in the embodiment described, the entire electrokinetic column 12 is not subjected to continuous current and continuous heating which is objectionable in the prior art. Additionally, the voltage which is applied between local electrodes E is substantially less than will be applied across the entire length of an electrokinetic column to separate the same particles of interest.

FIG. 3 illustrates an alternative embodiment of an element 18' including an electrode 20' and electrokinetic material 22'. The electrokinetic material 22' may be identical to the electrokinetic material 22 of FIG. 2. However, in FIG. 2, the electrode 20 was a porous screen-like construction which covers the entire flow area 14 and is permeable by the charged particles of interest. In FIG. 3, the electrode 20' is comprised of a plurality of thin strip electrodes 46 which connect to common bars 48, such that when a potential is applied to a common lead 50, that potential is present over the entire electrode 20'. As stated, elements 18' can substitute in the structure of FIG. 1 for any element 18. One advantage to the construction of element 18' is lower resistance to substance flow in the direction of the arrow 16.

In another alternative embodiment of the electrode elements 18' in accordance with the invention, the strip electrodes 46 are maintained independent of each other and from the common bars 48. In such an arrangement (FIG. 6), a separate lead connects to each strip electrode 46. It is possible to move particles of interest which are already within the electrokinetic material 22' of a segment 18' in the direction indicated by the arrow 52 (FIGS. 3, 6), by creating a traveling electrical field which moves in that direction from strip electrode 46 to strip electrode 46 until the particles of interest are not only concentrated within a given segment 18', but at one side or end of the segment.

Figure 6:
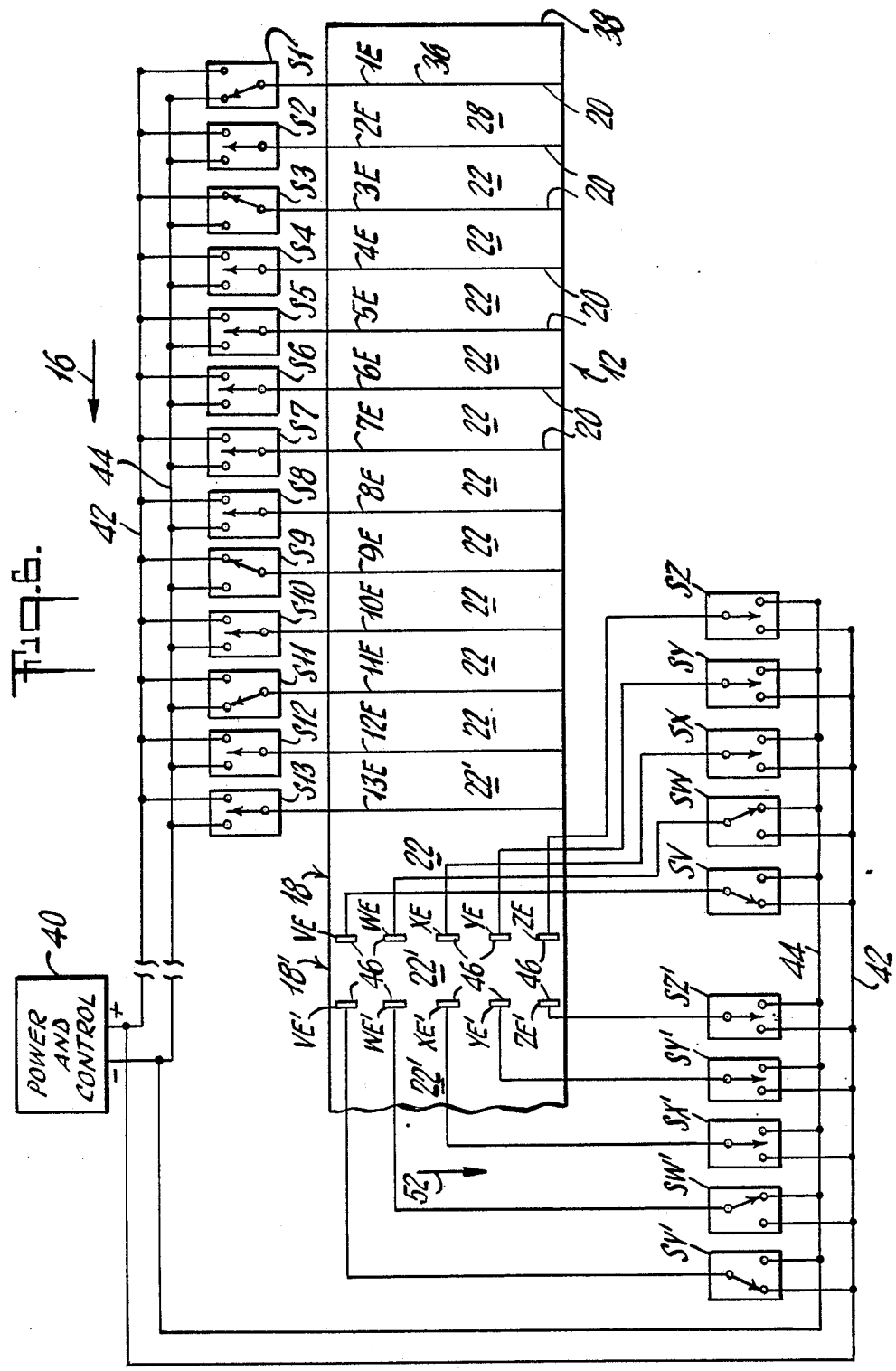
FIG. 6 is a semi-schematic and functional representation similar to FIGS. 5A-5C and including alternative segments of FIG. 3.

FIG. 6 illustrates the combination of segments 18, 18' into a system 10 and structure 11 similar to that shown in FIGS. 5A–5C. The construction and operation from electrodes 1E to electrode 13E are identical to that described above. However, following the segment 18 including the electrode 13E are segments 18' which include strip electrodes 46. For convenience, the strip electrodes 46 are identified as strip electrodes VE, WE, XE, YE, ZE and VE', WE', etc. These electrodes from two adjacent elements 18' are connected respectively to switches SV, SW, SX, SY and SZ and SV', SW', etc.

If as before, it is assumed that positively charged particles of interest are approaching electrode 13E, because of a negative potential (not shown) thereon through switch S13, then, motion of the particles can be continued by switching electrodes VE–ZE to connection with the negative bus 44 by setting the switches SV–SZ to positions connecting with the bus 44. At the same time electrode 13E is set into the neutral position and electrode 12E is connected to the positive bus 42.

As the positively charged particles approach the commonly connected strip electrodes VE–ZE, the negative potential is transferred to the strip electrodes VE'–ZE' by connecting the switches SV'–SZ' to the negative bus 44. At the same time, the switches SV–SZ are set to the neutral position and electrode 13E is switched to connect with the positive bus 42.

When the charged particles of interest are concentrated in the electrokinetic material 22' between the two rows of strip electrodes, the switches SV–SZ and SV'–SZ' are set to the neutral position and electrode 13E is set to the neutral position. Particle motion in the direction of the arrow 16 ceases.

Then, an electrical field wave is created in the direction indicated by the arrow 52. The first step is illustrated in FIG. 6 where electrodes VE and VE' are connected through the switches SV and SV' to the positive bus 42, while at the same time, the strip electrodes WE and WE' are connected through the switches SW and SW' to the negative bus 44. Thus, the positively charged particles travel toward the electrodes WE, WE'. To further advance the particles, the negative potential is switched (not shown) to the strip electrodes XE and XE', while the positive potential is moved to the strip electrodes WE and WE'. The electrical wave travels in a manner as described above, until the particles of interest are approaching the electrodes ZE and ZE'. At that time, all switches can be set to the neutral position and the segment 18' holding the particles of interest can be removed from the system 10.

As described, no intervening electrodes exist between the connected electrodes for motion in the direction of the arrow 52. However, any number of strip electrodes may be used as suits the dimensions of the apparatus and the number of intervening electrodes, if any, can vary to suit the application and to aid in determining velocity characteristics of the particles in the direction of the arrow 52.

FIG. 6 also illustrates a condition where more than one traveling wave of electrical potential is moving through the column 12 in the direction of the arrow 16 simultaneously, although spaced apart, in physical distance. Note that an electric field exists between electrodes 1E and 3E, while at the same time another remote electric field of opposite polarity orientation exists between electrodes 9E and 11E.

It should be noted that the traveling waves are spaced apart sufficiently so that the field of a wave has negligible effect on the following or leading waves. The velocities of the waves concurrently moving down the column 12 may differ, so long as physical interference between the waves is not created, and as stated previously, the polarity of a subsequent wave may differ from or be the same as its predecessor.

Although operation, as described above, of the system 10 in accordance with the invention has been accomplished by application of DC potential to the electrodes, other voltages can be applied to achieve separation of particles with certain advantages. Half-wave AC can be applied to the electrodes to create a traveling potential wave along the structure 12 as described above.

Figure 10:
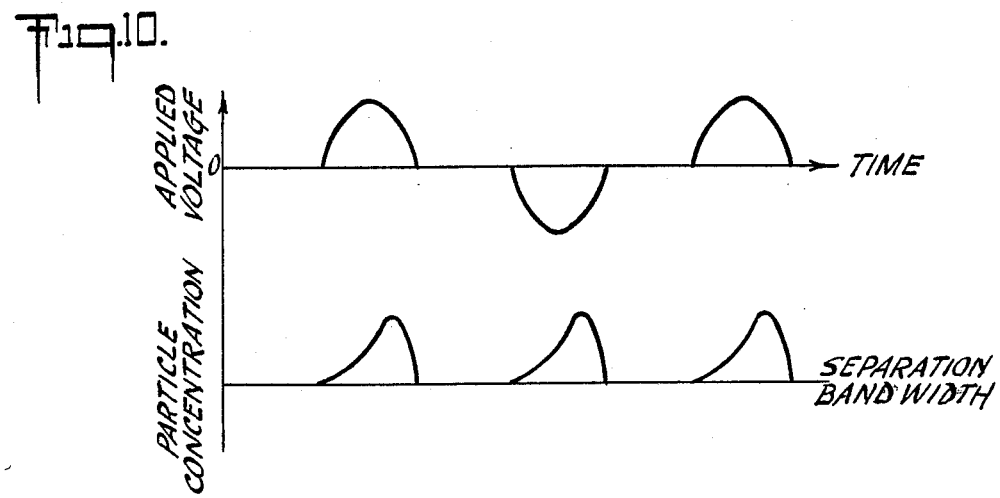
FIG. 10 illustrates gradients in particle density in separation zones produced by sine wave-type traveling waves in an electrokinetic separation system and method in accordance with the invention.

After a first traveling wave of one polarity has cleared the region of the input plenum 28, a next wave of opposite polarity may be initiated, such that oppositely charged particles, as compared to the first wave, are moved down the column (FIG. 10). The velocity of the potential wave along the column 12 generally will depend upon the AC voltage frequency or harmonics thereof. That is, the electrodes would be switched in connection each time the AC signal goes positive when separating negative particles, or every other time the signal goes positive, and so on. Using various waveshaping circuits, which are well-known in the art, it is possible to apply other waveforms to the busses 42, 44.

When using solid state switches, as discussed above, and where a plurality of DC voltages are available, it is possible under computer control to rapidly move from one voltage level to another, selecting from available voltages to produce any desired waveform. By selection of the proper waveform, a highly peaked, concentrated band of particles may be compressed into a narrow zone and collected in a single segment 18, 18'.

Figure 11:
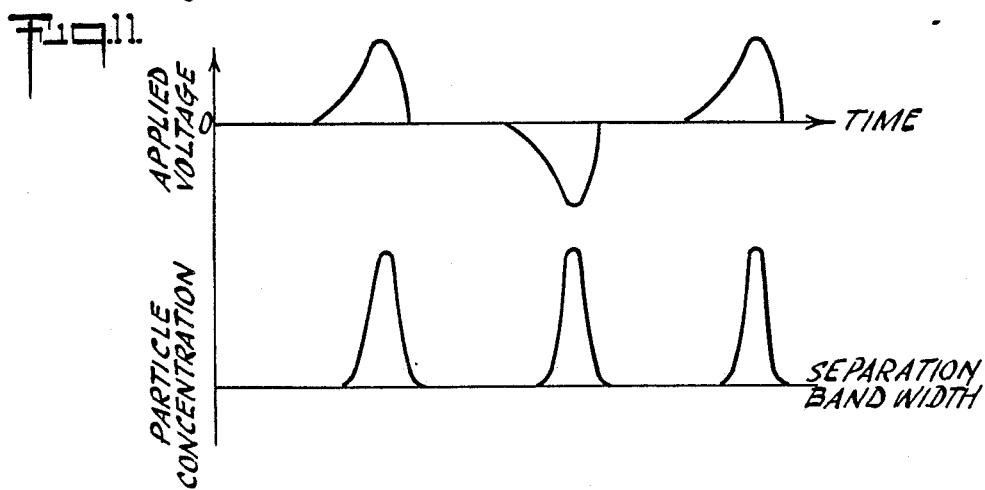
FIG. 11 illustrates a waveform providing narrower band definition and concentration of particles within the separation bands in an electrokinetic separation system and method in accordance with the invention.

As illustrated in FIG. 10, the particle concentration, as particles move in synchronism with the potential wave, has a skewed distribution and the width of the separation band is large with a long trailing edge when sine wave-type waveforms of FIG. 10 are applied. Desirably, the particles are separated into bands of narrow width. FIG. 11 illustrates a waveform for applied voltage to the electrodes which has a gradual rise time and a steep trailing edge. The result is a highly peaked, concentrated band of particles.

Figure 7:
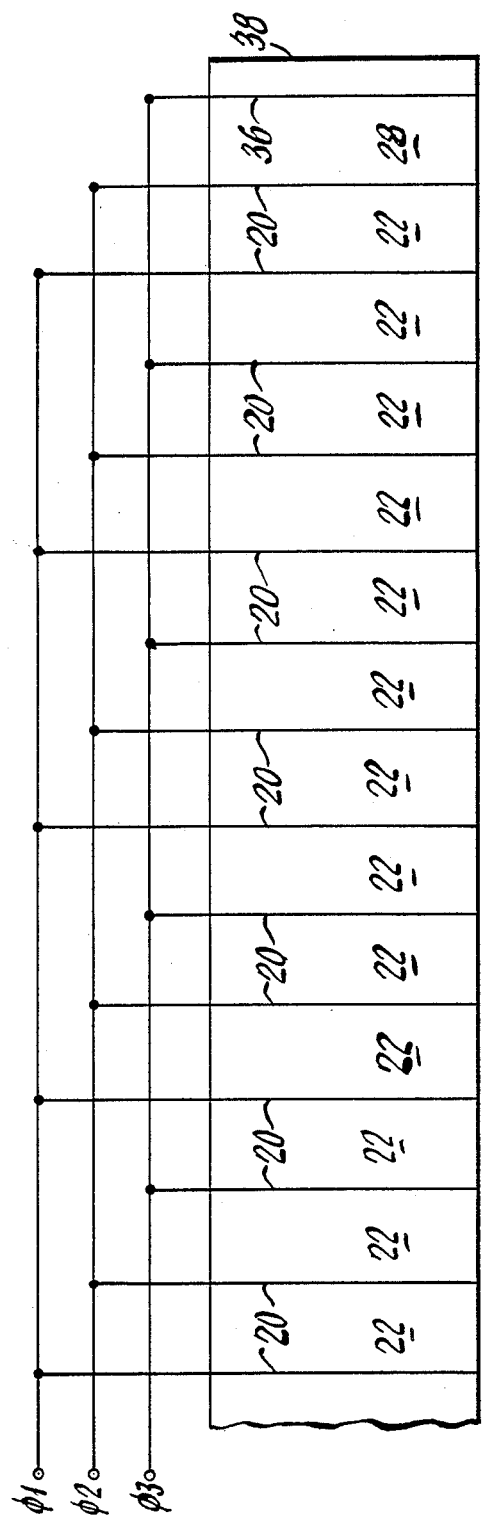
FIG. 7 is an alternative three-phase AC arrangement of the system in accordance with the invention.

FIG. 7 discloses an embodiment of the system 10 in accordance with the invention, where a three-phase power system is used to create the traveling potential waves. The electrodes are connected such that the first and fourth, second and fifth, third and sixth, etcetera, electrodes 20 are respectively connected to the same bus of the three-phase system. No switches are used intermediate the busses and the electrodes. The voltages between adjacent electrodes are 120° out of phase, with the result that a traveling wave of potential moves down the column 12 at a velocity which is directly related to the AC frequency and the electrode spacing. The waves alternate in polarity and the entire array of electrodes is energized at one time from one end of the member 12 to the other, unlike the embodiments described above.

Non-linear spacing of the electrodes in the three-phase array can alter the speed of the traveling wave over different portions of the column 12 along its length. Such electrode spacing is also applicable to the DC and AC voltages as described above to alter and select the velocity of the traveling wave or to provide desired gradients to the velocity.

It is also well-known in the art of electrokinetic separation of particles, that certain charged particles exhibit a changing charge dependent upon the pH of the medium in which the particles are placed. Thus, a particle which exhibits a negative charge at one pH may exhibit a positive charge at another pH value and a neutral charged condition, that is, no charge, at some intermediate pH value. Also, it is known that when a DC potential is placed across electrodes in contact with an electrolyte, a pH gradient is produced in the electrolysis cell between these electrodes. The electrode connected to the positive terminal has an acidic pH, that is, less than 7.0, whereas the electrode connected to the negative terminal of the power source produces a basic response, that is, a pH greater than 7.0. Thus, a gradient of pH values is formed within the electrolyte between the pH at one electrode and the pH at the other electrode.

Figure 8:
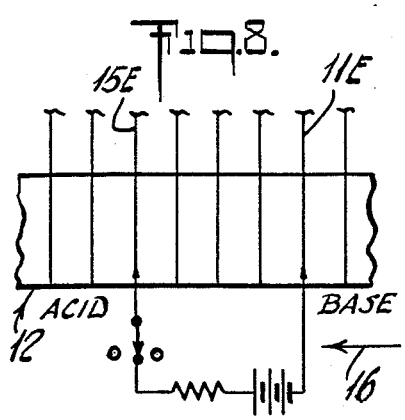
FIG. 8 is a fragmentary portion of a commercial electrokinetic separation system in accordance with the invention including isoelectric focusing to stop motion of particular charged particles in an electrokinetic column.
Figure 9:
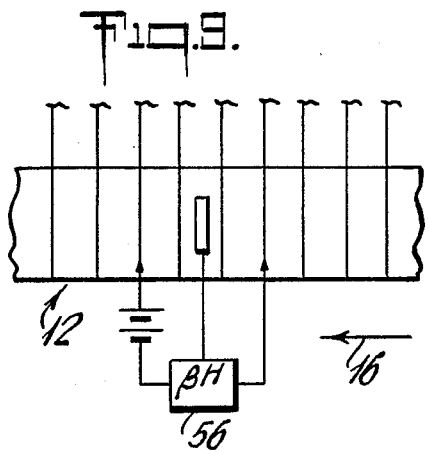
FIG. 9 is a semi-schematic illustration similar to FIG. 8 wherein isoelectric focusing and pH detection are utilized to bring a particular charged particle to a specific location and hold it there.

This isoelectric focusing and isotachophoresis are induced by the current applied to electrodes of an electrophoretic column 12, for example, between electrodes 11E and 15E (FIG. 8). A charged particle traveling in synchronism with the voltage potential wave will stop between the electrodes 11E, 15E, when between those electrodes there exists the pH value which causes the particle to lose its charge. An uncharged particle is not attracted to either the positive or negative electrode. Thus, it is possible in seeking to isolate known particles having known pH/charge characteristics, to create the proper pH conditions at a desired location. Thereby, a proper traveling voltage wave, moving with the proper phoretic speed, will separate the desired particle from the fluid and bring it to the spot where the pH is established which results in zero charge on that particle. This is especially useful where a fluid contains two different types of charged particles having the same polarity and phoretic speed. Where the charge/pH characteristics differ between these types of particles, it is then possible to separate them by using the amphoretic focusing technique illustrated in FIG. 8 to stop motion of at least one particle type. Also, as indicated in FIG. 9, by using a pH sensor 56, it is possible to locate where along the electrophoretic column 12 a pH is being produced by electrolysis which will create zero charge on a particular particle. Therefore, it is known where those particular particles will stop and be accumulated.

Thus, it can be seen that the constructions described above, are highly adaptable to many types of operation and power sources. The velocity of the traveling potential waves is controllable as is the effective length of the column 12.

It will thus be seen that the objects set forth above, among those made apparent from the preceding description, are efficiently attained and since certain changes may be made in carrying out the above method and in the constructions set forth, without departing from the spirit and scope of the invention, it is intended that all matters contained in the above description and shown in the accompanying drawings, shall be interpreted as illustrative and not in a limiting sense.

What is claimed is:

1. A commercial electrokinetic separation system for separating charged particles of different types and charges one from the other, said charged particles being separated from an inputted fluid, comprising:
   a plurality of layers of electrokinetic material;
   a plurality of column electrodes, said column electrodes being spaced apart one from the other in a first direction, one said electrokinetic material layer being positioned between each pair of said column electrodes, each said column electrode being in electrical contact with said adjacent electrokinetic material layers and subject to connection to a power source, said column electrodes and associated layers forming an electrokinetic column, a first column electrode at one end of said column being exposed to said fluid, an electric field being created in said electrokinetic column causing one of attraction and repulsion between selected ones of said column electrodes and respective types of said charged particles when said selected column electrodes are connected to said power source;
   a fluid chamber adjacent to said first column electrode at said one column end, said chamber being adapted to receive said fluid for contacting with said first column electrode; and
   a chamber electrode within said fluid chamber for contact with said fluid, said fluid being positioned between said chamber electrode and said first column electrode.

2. A commercial electrokinetic separation system as claimed in claim 1, and further comprising:
   switching means for selectively connecting said electrodes to said power source; and
   control means for regulating operation of said switching means and said connections between said electrodes and said power source.

3. A commercial electrokinetic separation system as claimed in claim 2, wherein said switching means includes a plurality of switches, each said electrode being associated with an individual switch connected at one end to said electrode and adapted at the other end for connection to said power source, said control means selectively regulating operation of each switch.

4. A commercial electrokinetic separation system as claimed in claim 3, wherein said switch is functionally at least a single pole, three-position switch adapted to connect said electrode to either line of a two-line power source, or to maintain an unconnected condition for the associated electrode based upon three positions of the switch.

5. A commercial electrokinetic separation system as claimed in claim 2 for operation from a DC voltage source, said control means regulating said switching means to connect a first pair of said electrodes to one line each of said DC source, said electric field being created between said first pair of connected electrodes, said control means being adapted to remove said connections at a selected time interval from said first electrode pair and apply DC line connections across a second pair of electrodes in said plurality of electrodes, said electrical field becoming established between said second pair of electrodes and ceasing between said first pair of electrodes, said second pair being connected so said field maintains the same polarity, said electrical field being moved away from said one end of said electrokinetic column in said first direction of electrode spacing by said switching of DC voltage.

6. A commercial electrokinetic separation system as claimed in claim 5, wherein the electrodes of said first and second electrode pairs respectively are separated one from the other by at least one intervening electrode.

7. A commercial electrokinetic separation system as claimed in claim 6, wherein within each said pair the number of intervening electrodes is one and the intervening electrode between said first pair of electrodes is an electrode of said second pair, and the intervening electrode between said second pair of electrodes is an electrode of said first pair, said DC voltage being applied by said control and switching means to consecutive electrode pairs, moving said electrical field wavelike in said first direction.

8. A commercial electrokinetic separation system as claimed in claim 7, wherein the number of said electrode pairs with at least one intervening electrode is n, said control means being adapted to switch said DC voltage, and said wave-like field travels, from said first pair to any selected pair between said first and said nth pair, the selection of pairs, the order and timing of switching being programmably controlled by said control means.

9. A commercial electrokinetic separation system as claimed in claim 6, wherein an intervening electrode is always isolated from the power source, said power source-isolated electrode serving to align the electric field.

10. A commercial electrokinetic separation system as claimed in claim 5, wherein said control means is adapted to reverse the polarity of said DC voltage source, particles of either positive or negative polarity being selectively separable in the separation system.

11. A commercial electrokinetic separation system as claimed in claim 5, wherein said control means alternately applies electrical potentials of opposite polarity to said electrode pairs creating traveling electrical fields of opposite polarity in said electrokinetic column, said traveling fields being separated in time and along the length of said electrokinetic column.

12. A commercial electrokinetic separation system as claimed in claim 5, wherein said power source provides at least one of a variety of DC levels and AC waveforms, said control means being adapted to regulate operation of said switching means providing selectable polarity and selectable waveforms to said electrodes.

13. A commercial electrokinetic separation system as claimed in claim 10, wherein said electrodes are one of uniformly and non-uniformly spaced along the length of said electrokinetic column, the thickness of said layers being varied to accommodate the spaces between electrodes.

14. A commercial electrokinetic separation system as claimed in claim 1, and further comprising a focusing element said focusing element comprising means for applying a DC potential between a pair of said electrodes, said DC potential creating a pH gradient in said electrokinetic column between said connected electrodes, charged particle having charges variable in magnitude and polarity with pH coming to rest from motion in said one direction at a position along said column where the induced pH results in zero charge on said particle.

15. A commercial electrokinetic separation system as claimed in claim 14, and further comprising a pH detector sensing pH between said focusing element electrodes, a selectable pH at a selected location between said focusing element electrodes being achieved by varying the applied DC potential and resultant current.

16. A commercial electrokinetic separation system as claimed in claim 1, wherein said electrokinetic column is an electrophoretic column, said layers being formed of electrophoretic material.

17. A commercial electrokinetic separation system as claimed in claim 8, wherein said electrokinetic column is an electrophoretic column, said layers being formed of electrophoretic material.

18. A commercial electrokinetic separation system as claimed in claim 10, wherein said electrokinetic column is an electrophoretic column, said layers being formed of electrophoretic material.

19. A commercial electrokinetic separation system as claimed in claim 1, wherein said power source is AC three-wire, three-phase, the first, fourth, seventh . . . electrodes of said plurality of electrodes being connected to the first wire of said three-phase source, the second, fifth, eighth . . . electrodes of said plurality of electrodes being connected to the second wire of said three-phase source, the third, sixth, ninth . . . electrodes of said plurality of electrodes being connected to the third wire of said power source, traveling electrical fields being created in said electrokinetic column, said fields traveling from said one end in said first direction, one traveling wave of one polarity following another of opposite polarity, the repetition rate of said traveling fields being dependent upon the AC frequency, the velocity of said fields along said electrokinetic column being dependent upon said AC frequency and the spacing between said electrodes.

20. A commercial electrokinetic separation system as claimed in claim 19, wherein said electrodes are one of uniformly and non-uniformly spaced apart one from the other in said first direction.

21. A method of separating charged particles from an inputted fluid using a commercial electrokinetic separation system including an electrokinetic column having a plurality of layers of electrokinetic material, a plurality of column electrodes, said column electrodes being spaced apart one from the other in a first direction, one said electrokinetic material layer being between each pair of said column electrodes, each said column electrode being in electrical contact with said adjacent electrokinetic material layers, a first electrode at one end of said column being exposed to said fluid, and a fluid chamber adjacent to said first electrode at said one column end, said chamber being adapted to receive said fluid for contacting with said first electrode, and a chamber electrode within said fluid chamber, said fluid being positioned between said chamber electrode and said first electrode of said column, comprising the steps:

(a) inputting said fluid into said chamber;
(b) connecting the D.C. voltage source between said chamber electrode and a column electrode creating an electrical field therebetween and drawing charged particles from said fluid into said column;
(c) maintaining said connections for a period of time;
(d) connecting the DC voltage source across a first pair of said column electrodes at said one end, an electrical field being created between said connected column electrodes, charged particles in said intervening electrokinetic material being attracted toward said connected electrodes;
(e) maintaining said connections for a period of time;
(f) unmaking the connections of step (d) as charged particles of interest approach the column electrode of said first pair farthest from said one end of said electrokinetic column;
(g) connecting a second pair of column electrodes to said DC source, said second pair of column electrodes straddling said particles of interest and creating a field having the same polarity as that created by said first pair of column electrodes, said particles of interest being attracted to the column electrode of said second pair farthest from said one end.

22. A method as claimed in claim 21 and further comprising the steps of repeating steps (d),(e),(f) above, with a third, fourth, fifth . . . nth pair of column electrodes respectively along the length of said electrokinetic column as required to separate said particles of interest from said fluid into a separation band.

23. A method as claimed in claim 22, wherein at least one unconnected column electrode intervenes the electrodes of said connected pairs.

24. A method as claimed in claim 23, wherein said DC source has two lines and said connected column electrode pairs have one intervening column electrode, said second column electrode pair being formed by moving the connection to each of said two DC lines by one column electrode, respectively, in said one direction away from said one end where said fluid is inputted.

25. An electrokinetic separation system as claimed in claim 1, wherein said power source is AC n wire, poly-phase, the first, $1+n$, $1+2n$, . . . column electrodes of said plurality of electrodes being connected to the first wire of said poly-phase source, the second, $2+n$, $2+2n$, . . . column electrodes of said plurality of electrodes being connected to the second wire of said poly-phase source, the third, 3+n, 3+2 n ... column electrodes of said plurality of electrodes being connected to the third wire of said power source, etc. to the nth column electrode connected to the nth wire, traveling electrical fields being created in said electrokinetic column, said fields traveling from said one end in said first direction, one traveling wave of one polarity following another of opposite polarity, the repetition rate of said traveling fields being dependent upon the AC frequency, the velocity of said fields along said electrokinetic column being dependent upon said AC frequency and the spacing between said column electrodes.

26. A commercial electrokinetic separation system as claimed in claim 25, wherein an intervening electrode is always isolated from the power source, said power source-isolated electrode serving to align the electric field.

27. A commercial electrokinetic separation system as claimed in claim 26, wherein said electrodes are one of uniformly and non-uniformly spaced apart one from the other in said first direction.

28. A commercial electrokinetic separation system as claimed in claim 1, wherein said electrokinetic column is of extended length, and further comprising a plurality of strip electrodes spaced apart one from the other in a second direction, said strip electrodes being positioned along the column length beginning at a selected distance.

29. A commercial electrokinetic separation system as claimed in claim 28, and further comprising:
switching means for selectively connecting said strip electrodes to said power source; and
said control means regulating operation of said switching means and said connections between said strip electrodes and said power source.

30. A commercial electrokinetic separation system as claimed in claim 29, wherein said switching means includes a plurality of switches, each said strip electrode being associated with an individual switch connected at one end to said electrode and adapted at the other end for connection to said power source, said control means selectively regulating operation of each switch.

31. A commercial electrokinetic separation system as claimed in claim 30, wherein said switch is functionally at least a single pole, three-position switch adapted to connect said strip electrode to either line of a two-line power source, or to maintain an unconnected condition for the associated strip electrode based upon three positions of the switch.

32. A commercial electrokinetic separation system as claimed in claim 29 for operation from a DC voltage source, said control means regulating said switching means to connect a first pair of said strip electrodes to one line each of said DC source, said electric field being created between said first pair of connected strip electrodes, said control means being adapted to remove said connections at a selected time interval from said first strip electrode pair and apply DC line connections across a second pair of strip electrodes in said plurality of strip electrodes, said electrical field becoming established between said second pair of strip electrodes and ceasing between said first pair of strip electrodes, said second pair being connected so said field maintains the same polarity, said electrical field being moved transversely within said electrokinetic column by said switching of DC voltage, charged particles being movable with separation in said first direction to said selected lengthwise position of said column and subsequently movable in said transverse second direction for concentration.

33. A method of separating charged particles from an inputted fluid using a commercial electrokinetic separation system including an electrokinetic column having a plurality of layers of electrokinetic material, a plurality of column electrodes and strip electrodes, said column electrodes being spaced apart one from the other in a first direction, said strip electrodes being spaced apart in a second transverse direction, one said electrokinetic material layer being between each pair of said column and strip electrodes, each said column and strip electrode being in electrical contact with said adjacent electrokinetic material layers, a first column electrode at one end of said column being exposed to said fluid, and a fluid chamber adjacent said first column electrode at said one column end, said chamber being adapted to receive said fluid for contacting with said first column electrode, and a chamber electrode within said fluid chamber, said fluid being positioned between said chamber electrode and said first column electrode comprising the steps:

(a) inputting said fluid into said chamber;
(b) connecting the D.C. voltage source between said chamber electrode and a column electrode creating an electrical field therebetween and drawing charged particles from said fluid into said column;
(c) maintaining said connections for a period of time;
(d) connecting the DC voltage source across a first pair of said column electrodes at said one end, an electrical field being created between said connected column electrodes, charged particles in said intervening electrokinetic material being attracted toward said connected electrodes;
(e) maintaining said connections for a period of time;
(f) unmaking the connections of step (d) as charged particles of interest approach the column electrode of said first pair farthest from said one end of said electrokinetic column;
(g) connecting a second pair of column electrodes to said DC source, said second pair of column electrodes straddling said particles of interest and creating a field having the same polarity as that created by said first pair of column electrodes, said particles of interest being attracted to the column electrode of said second pair farthest from said one end.

34. A method as claimed in claim 33 and further comprising the steps of repeating steps (d),(e),(f) above, with a third, fourth, fifth ... nth pair of column electrodes respectively along the length of said electrokinetic column as required to separate said particles of interest from said fluid into a separation band and bring said particles to said strip electrodes.

35. A method as claimed in claim 34 and further comprising the steps:

1. connecting a first pair of said strip electrodes to one line each of said DC source, said electric field being created between said first pair of connected strip electrodes;
2. unmaking said connections from said first strip electrode pair at a selected time interval;
3. applying DC line connections across a second pair of strip electrodes in said plurality of strip electrodes, said electrical field becoming established between said second pair of strip electrodes and ceasing between said first pair of strip electrodes, said second pair being connected so said field maintains the same polarity, said electrical field being moved transversely within said electrokinetic column by said switching of DC voltage, charged particles being movable with separation in said first direction to a selected lengthwise position of said column and subsequently being movable in said transverse second direction for concentration.

36. A method as claimed in claim 35 and further comprising the steps of repeating steps 1,2,3 above, with a third, fourth, fifth . . . nth pair of strip electrodes along said second direction as required to concentrate said separation band in a selected region of said column.

* * * * *